United States Patent [19]

Argabrite et al.

[11] 4,196,616
[45] Apr. 8, 1980

[54] MULTIPOSITIONABLE SUPPORT MEANS FOR A HARDNESS TESTER

[75] Inventors: George A. Argabrite, Malibu; William C. Sanford, Woodland Hills, both of Calif.

[73] Assignee: Pacific Transducer Corporation, Los Angeles, Calif.

[21] Appl. No.: 946,773

[22] Filed: Sep. 28, 1978

[51] Int. Cl.² .................. G01N 3/44; G01D 11/30
[52] U.S. Cl. ............................... 73/81; 33/169 B; 33/DIG. 1; 248/289 R
[58] Field of Search ............... 73/818, 81; 335/285, 335/295; 248/206 A, 289 R, 291, 122; 33/DIG. 1, 169 R, 169 B, 21 C

[56] References Cited

U.S. PATENT DOCUMENTS

| | | | |
|---|---|---|---|
| 2,280,437 | 4/1942 | Levesque | 335/295 |
| 2,466,567 | 4/1949 | Williams | 73/81 |
| 2,544,205 | 3/1951 | Williams | 73/81 |
| 2,791,031 | 5/1957 | Uskert | 33/21 C |
| 2,888,617 | 5/1959 | Baumet | 335/295 |
| 3,089,066 | 5/1963 | Uc et al. | 335/295 |
| 3,910,538 | 10/1975 | Baitella | 248/122 |

Primary Examiner—Gerald Goldberg
Assistant Examiner—Joseph W. Roskos
Attorney, Agent, or Firm—William W. Glenny

[57] ABSTRACT

A support for a hardness testing device, the support being capable of positioning the hardness testing device to measure hardness of a surface in different positions. The multipositionable support comprises a pair of elongated parallel support members along which is supported a slidably adjustable cross-beam member for positioning a hardness device relative to a surface being tested. Each support member has pivotally connected to one of its ends a magnetic means which may be moved about its pivotal axis and rotated about the axis of its support member for alignment of the magnet means with an adjacent supporting surface. The magnet means has sufficient holding power to fixedly and rigidly hold the support against the force applied to the indentor of the testing device. The hardness testing device is coupled to an actuator knob at the cross-beam and is supported at the cross-beam.

8 Claims, 7 Drawing Figures

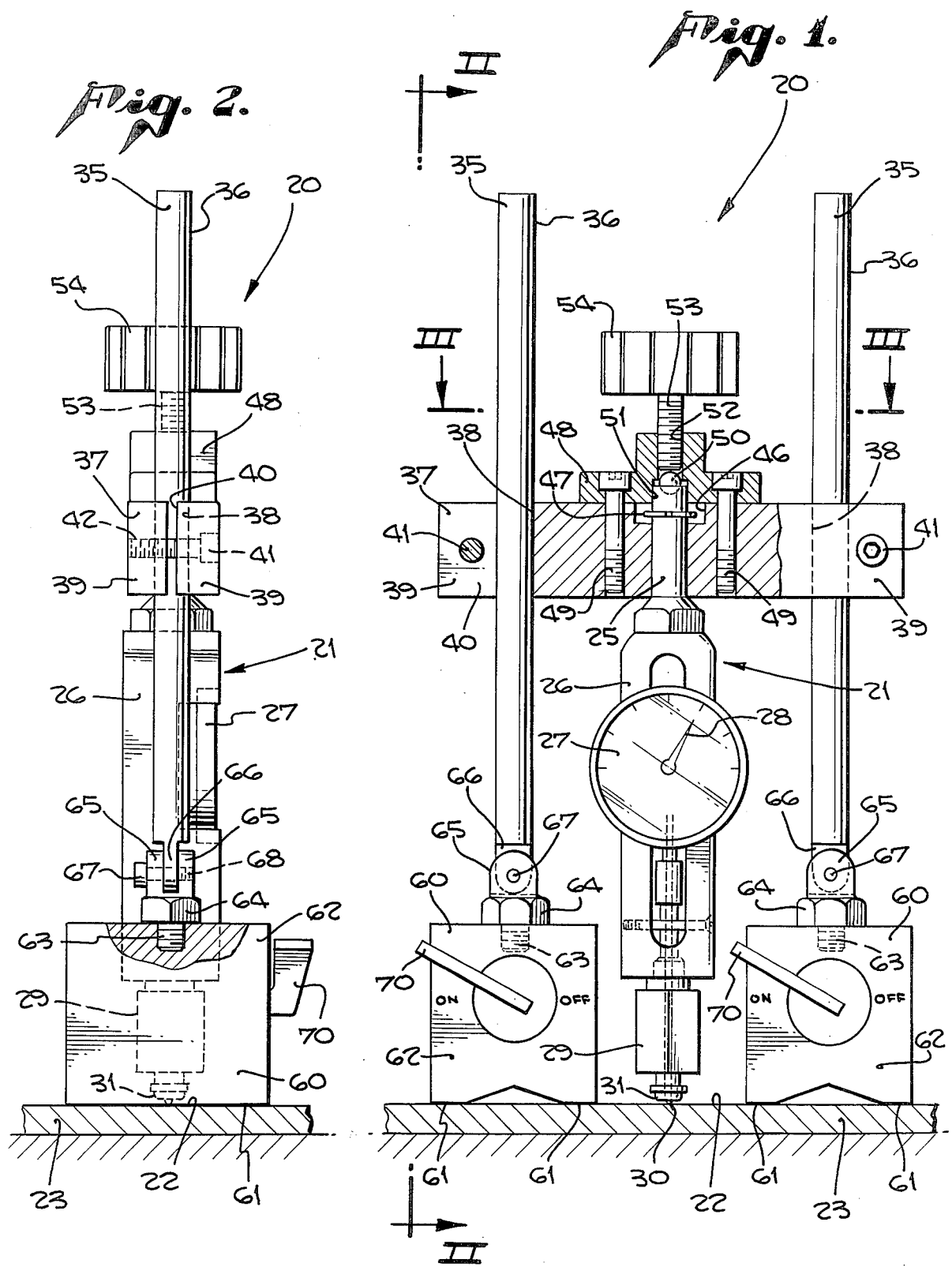

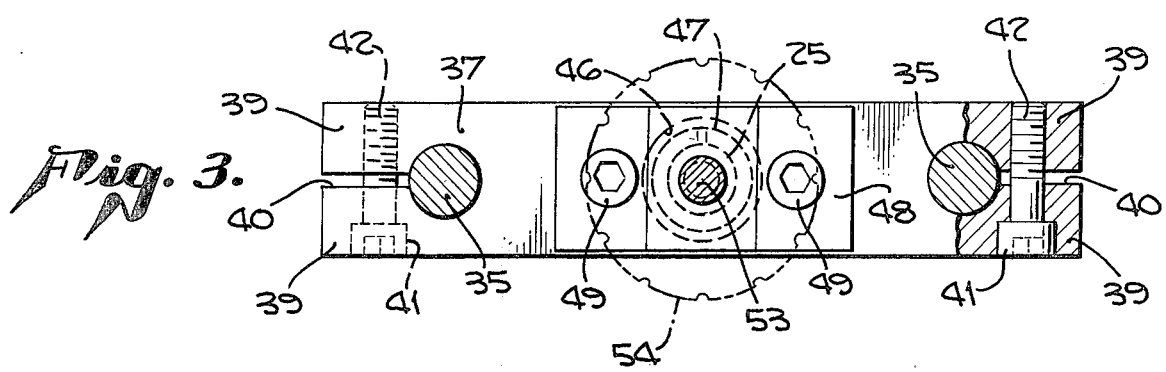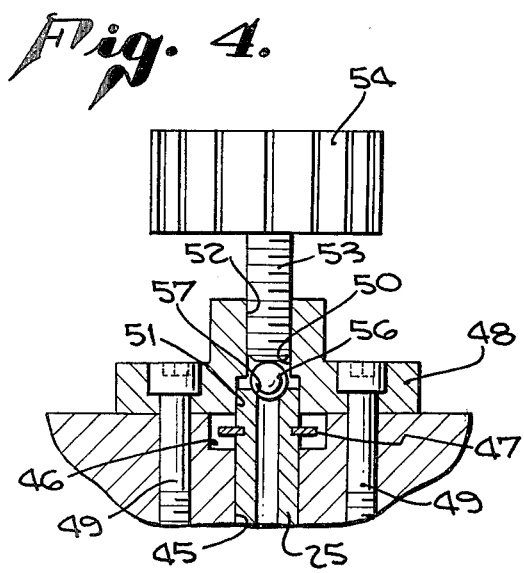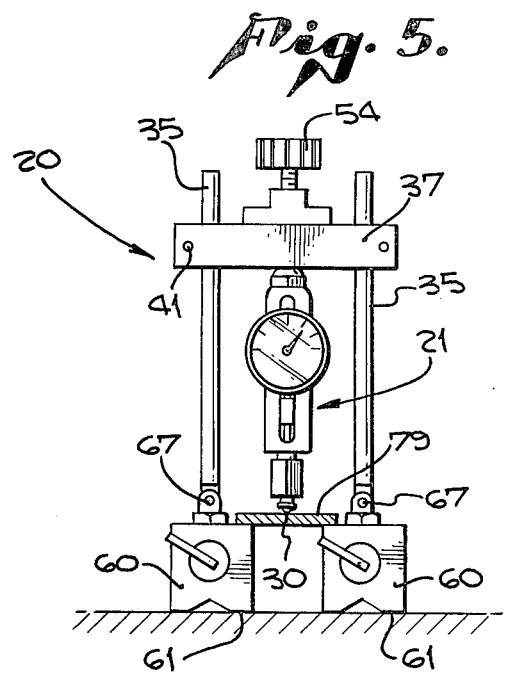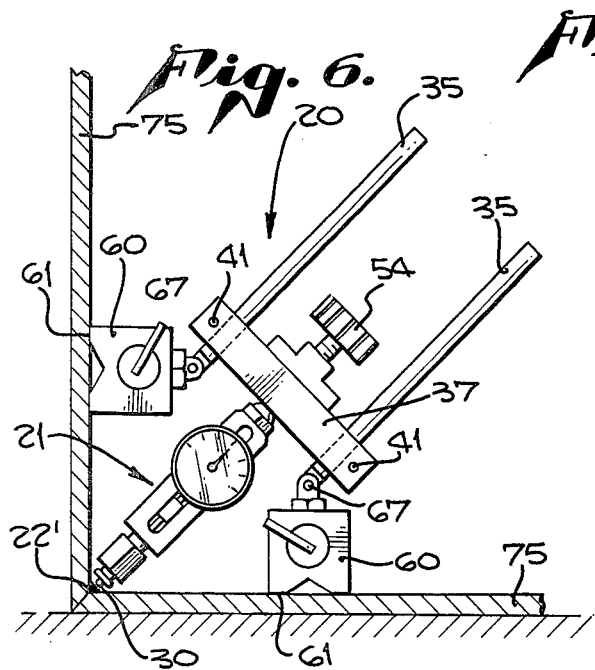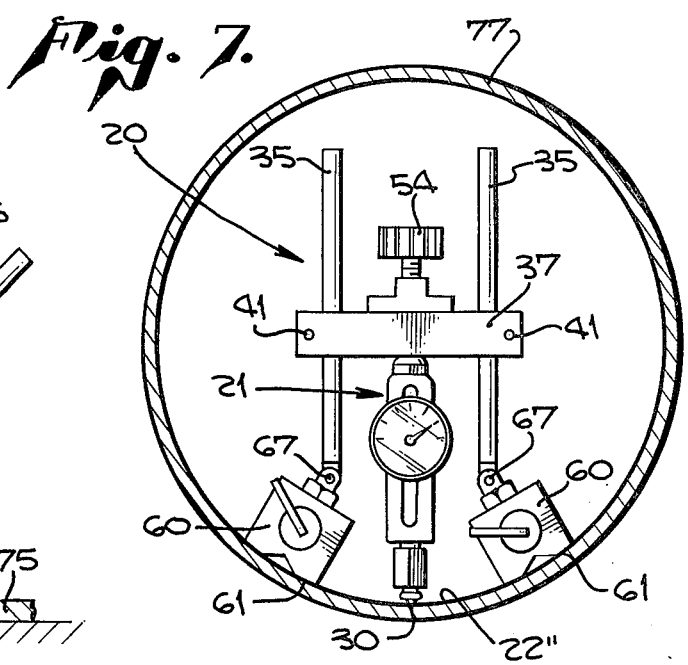

MULTIPOSITIONABLE SUPPORT MEANS FOR A HARDNESS TESTER

BACKGROUND OF INVENTION

In the testing of hardness of materials, various types of jigs are used to hold a hardness testing device in proper relationship with the surface whose hardness is to be tested. Such a jig might include a drill press or other well-known tool holding apparatus which permit the testing device to be positioned perpendicularly to the surface being tested and to apply a preselected force to the test surface through an indentor, such as a steel ball, diamond, or point. The use of conventional jigs for holding testing devices generally do not permit the convenient positioning of the testing device in proper relation to a surface to be tested when the surface is other than a planar surface, as for example inside and outside surfaces of a pipe, weld material at the juncture of plates arranged at 90° to each other, and other convex and concave configurations.

SUMMARY OF INVENTION

The present invention relates to a versatile, multipositional, portable support apparatus for a hardness tester wherein the hardness tester may be readily positioned to measure hardness on any ferromagnetic surface in almost any position of the surface. The present invention contemplates a support apparatus for a hardness tester device wherein the hardness tester device can be properly positioned and aligned with a surface being tested; that is, in 90° relationship thereto and touching the surface and is readily adaptable to provide a rigid fixed support with respect to various configurations of supporting surfaces adjacent to the surface whose hardness is to be measured.

The invention generally contemplates a support apparatus for mounting a hardness testing device in which spaced magnetic means have contact faces for alignment and magnetic seating on support surfaces adjacent to surface to be tested, and support members adjustably connected to the magnetic means for supporting and positioning the hardness testing device in operable relation to the surface to be tested. The support members slidably adjustably carry a cross-beam having means for a drive coupling connection to the hardness testing device.

The primary object of this invention, therefore, is to provide a portable, multipositionable, support apparatus for a hardness testing device and readily adaptable to variable surface conditions.

An object of the present invention is to provide a novel support apparatus for a hardness testing device in which the support apparatus is attachable to supporting surfaces by magnetic means.

Another object of the present invention is to provide a novel support apparatus in which the hardness testing device carried thereby is readily operably positioned with respect to a surface to be tested.

A general object of the present invention is to provide a support apparatus for a hardness testing device in which adjustment of the device is provided in directions toward and away from the surface to be tested. The support apparatus includes attachment means pivotally movable about an axis transverse to the longitudinal axis of the hardness device and also movable in rotation about a longitudinal axis parallel to the hardness device.

The present invention contemplates a support apparatus for a hardness testing device which is portable, readily installed in a variety of conditions of support surfaces, and provides means coupled to the hardness testing device to permit convenient operation of the device.

Various other objects and advantages of the present invention will be readily apparent from the following description of the drawings in which an exemplary embodiment of the support apparatus of this invention is shown.

IN THE DRAWINGS

FIG. 1 is a front elevational view, partly in section, of a support means for a hardness testing device embodying this invention.

FIG. 2 is a side view of the support means shown in FIG. 1, the view being taken from the plane indicated by line II—II of FIG. 1.

FIG. 3 is a transverse sectional view taken in the plane indicated by line III—III of FIG. 1.

FIG. 4 is an enlarged, fragmentary, sectional view taken in the same plane as the partial section shown in FIG. 1.

FIG. 5 is a reduced front view of the support means shown in FIG. 1 illustrating use of the support means for calibration of the testing device.

FIG. 6 is a front view of the support means of this invention positioned to measure hardness of a fillet weld at the interior vertex of an included angle formed by two plates at 90° to each other.

FIG. 7 is a view of the support means of this invention positioned within a cylindrical pipe for measuring hardness of an interior surface of said pipe.

Referring first to FIG. 1 of the drawings, a multipositionable support means embodying this invention is generally indicated at 20. Support means 20 has cooperably associated therewith a hardness testing device 21 for measuring the hardness of a surface 22 of an exemplary plate member 23.

Hardness testing device 21 may be any testing device of well-known manufacture and of the type shown in the drawing. Testing device 21 generally includes a connector spindle member 25 extending above an elongated body member 26 upon which is mounted a suitable scale 27, such as a Rockwell B or C Scale which includes indicia indicating hardness of a surface being tested. An indicator 28 is associated with a load cell 29 which may extend upwardly into the body member 26 and houses a precision spring, not shown, which preloads the indentor 30 below the load cell 29. The indentor 30 may be made of hardened steel and may be ground to a selected shape, an exemplary shape including an angle of 30° and a tip ground to a 0.012 inch radius. The indentor normally extends slightly beyond a circular base element 31 provided below load cell 29. It will be understood that hardness testing device 21 may include any testing device of well-known manufacture and the detail construction of device 21 is not part of this invention.

Support means 20 may comprise a pair of elongated parallel support members 35, preferably made of stainless steel with precisely machined, polished, external, cylindrical surfaces 36. A cross-beam member 37 is provided with spaced throughbores 38 for slidable reception of support members 35 for adjustment of the position of cross-beam 37 so that testing device 21 properly contacts test surface 22. Such slidable adjustment of cross-beam member 37 is provided by spaced split end portions 39 at each end of beam member 37. Adjacent end portions 39 are separated by a slot 40 extending from bore 38 and a suitable cap screw 41 has threaded engagement at 42 with one end portion 39 so that the adjacent end portions 39 may be drawn together to secure cross-beam 37 in selected position on support members 35 or may be drawn apart to permit convenient adjustment of the cross-beam 37 along the longitudinal axes of support members 35.

Centrally, between support members 35, beam member 37 may be provided with a through opening 45 with an enlarged top circular recess 46 for slidably receiving the connector spindle member 25 of testing device 21. In this example, connector member 25 includes a retainer ring 47 received within an annular groove in spindle member 25 so that the testing device 21 will remain assembled with cross-beam 37.

Cross-beam member 37 carries a cap member 48 secured to beam member 37 by a pair of cap screws 49. Cap member 48 includes a through opening 50 aligned with the axis of opening 45, said opening 50 having a lower portion 51 for reception of the top of connector member 25. The upper portion of through opening 50 is internally threaded as at 52 for threaded engagement with the externally threaded shank 53 of an actuator drive knob 54. Between the end face of threaded shank 53 of drive knob 54 and the upper end of connector member 25 is provided a hardened steel ball 56 seated on a tapered annular surface 57 coaxial with the axis of connector member 25. The steel ball 56 provides a low frictional coupling means between the actuator drive knob 54 and the testing device 21, the operation of which is hereinafter described.

At the lower ends of support members 35 are provided multipositionable magnetic means 60, each provided with spaced magnetic contact faces 61 for engagement with a supporting surface. Each magnetic means 60 includes a block 62 of magnetic material having, at the center of its upper surface, a threaded bore 63 provided a threaded connection with a clevis nut 64. Clevis nut 64 includes upstanding spaced clevis elements 65 between which is received a bottom end fitting 66 of support member 35. A suitable cap screw 67 extends through a clevis element 65, and fitting 66 for threaded engagement as at 68 with the other clevis element 65 so that the magnetic means 60 is provided a pivotal mounting about the axis of cap screw 67. Cap screw 67 is adapted to be loosened to permit convenient continuous pivotal motion of magnetic means 60 about its axis to properly seat the magnetic faces 61 against a surface. When seated, the cap screw 67 may be tightened to maintain the angular relationship of the magnetic means 60 with the longitudinal axis of support member 35.

From the above description, it will be readily apparent that when the testing device 21 is assembled with the cross-beam member 37, the indentor 30 of the testing device 21 may be readily moved away or toward the test surface 22 by loosening cap screws 41 and slidably adjusting cross-beam member 37 on the support members 35. When the indentor touches the surface to be measured and device 21 is perpendicular to the surface 22 being tested, the magnetic means 60 may be adjusted about the pivot axis of cap screws 67 and/or rotated about the axis of its associated support member 35 so that contact faces 61 are properly aligned and seated on the supporting surface. When both magnetic means have been so adjusted, the magnetic units may be energized by moving switch arm 70 to "On" position. Cap screws 67 and 41 are then tightened to provide a rigid stand for device 21. The magnetic means may provide an exemplary holding force of about 250 lbs. to hold and retain the support means on the supporting surface.

When the testing device 21 is first brought into contact with test surface 22, drive actuator knob 54 should be in upper retracted position so that retainer ring 47 or the end face of the connector member 25 lightly touches the opposed surfaces of cap member 48.

Hardness of the test surface 22 may then be measured by rotating the drive knob 54 clockwise to move device 21 downwardly through the ball coupling arrangement provided between the end of the knob shank 53 and the top end face of cylindrical spindle member 25. Moving device 21 downwardly will cause the circular base element 31 to move into contact with the test surface 22 and to also move and load the indentor which has been previously calibrated and which may exert an exemplary force of 85 lbs. on the test surface. The dial scale and dial indicator 28 will then show the Rockwell B Scale hardness. The force applied through the drive actuator knob 54 and the load cell 29 is approximately 85 lbs. The holding power of the magnetic means on the stand is approximately 250 lbs. The support stand is, therefore, sufficiently fixed and rigid to permit taking of accurate hardness readings.

The versatility of the support means 20 is illustrated in FIGS. 6 and 7. In FIG. 6, it is desired to measure the hardness of the surface of a fillet weld 22' located along the joint line of two plates 75 disposed at 90° to each other. Cross-beam 37 has been advanced along the support members 35 almost to the lower ends of support members in order to advance the device 21 into a position for necessary contact with the weld surface 22'. Magnetic means 60 are readily pivoted about the axes of cap screw 67 so that their magnetic faces 61 may readily engage plates 75. The axis of device 21 is substantially perpendicular to the surface 22' of the weld to be tested. After the support means is properly positioned and the magnetic means turned on to magnetically retain the stand in the desired position, the cap screws 41 and 67 are tightened and drive actuator knob 54 may be turned to actuate the hardness testing device 21 in a manner similar to that described above.

From FIG. 6 it will be apparent that the stand may be positioned to accommodate other angular variations of plates 75 by adjustment of the cross-beam 37 along the support members 35 and the adjustment of magnetic means 60 to provide proper alignment of the hardness testing device 21.

In FIG. 7 a further example of the adjustability of support means 20 is illustrated and demonstrates the taking of a hardness reading on the interior surface of a cylindrical pipe member within which the hardness device is positioned. The height of support means 20 may be approximately 9½" and its width approximately 6". Because of the angular adjustability of the magnetic means 60 with respect to the support members 35, the support means of this invention may be used within pipes of 8" or greater inside diameter.

In FIG. 7 it will be readily apparent that the cross-beam 37 has been positioned on support members 35 in still another location and that the magnetic means 60 are angularly positioned against the interior cylindrical surface of the pipe 77 so that the indentor 30 may be brought into proper contact with the interior surface 22" being tested and with the axis of device 21 lying along a diameter of pipe 77. The operation of the testing device and the stand is similar to that described above.

FIG. 7 illustrates the use of the support means on an interior cylindrical surface. The support means may also be used on an exterior cylindrical surface and convex surfaces. The support means thus permits hardness measurements to be made on ferromagnetic surfaces of many varying configurations, as long as the magnet means are alignable with adjacent supporting surfaces.

It will be understood that the magnetic means 60 are of a type and manufacture adapted to be energized to provide a suitable selected magnetic holding power, as for example 250 lbs. Preferably, the magnet means achieves its maximum holding power on smooth, unpainted ferromagnetic surfaces. In the event the supporting surfaces are painted or irregular or rough, the supporting surfaces may have to be cleaned or ground to achieve the desired holding power.

FIG. 5 illustrates the use of the support stand of this invention for calibration of the test device 21. In such calibration, a test block 79 having a known hardness may be supported on magnetic means 60 between support members 35 and the cross-beam member 37 raised so that the hardness testing device 21 may be properly positioned with its indentor 30 touching the surface of test block 79. The actuator knob 54 of the device 21 is turned until the base 31 is bottomed on the surface of the test block. The bezel or rim of the gauge is then turned until the known test block hardness reading or indicia is directly under the gauge pointer or indicator. The test device 21 is thus calibrated and reads the hardness of test block 79. It will be understood that the hardness testing device 21 may be calibrated by other means, FIG. 5 illustrating a further use of the support means of this invention.

Various changes and modifications of the support means described above may be made which come within the spirit of this invention and all such changes and modifications coming within the scope of the appended claims are embraced thereby.

We claim:

1. A multipositionable support means for a hardness testing device for measuring the hardness of a surface in different positions, comprising:
    a pair of elongated parallel support members having longitudinal axes;
    a cross-beam member interconnecting said support members and slidably adjustable along said support members and adapted to selectively position said hardness testing device relative to a surface being tested;
    a magnetic means connected to each support member and adjustable relative to the axis of the support member and adapted to position the hardness testing device normal to the surface being tested; and
    means carried by said cross-beam member adapted to support said hardness testing device between said parallel support members.

2. A support means as stated in claim 1 wherein
    each of said magnetic means is pivotally mounted about an axis extending laterally with respect to the axis of said support member.

3. A support means as stated in claim 2 wherein
    each of said magnetic means is rotatable about the axis of its associated support member.

4. In a support means as stated in claim 1 wherein
    each of said magnetic means includes spaced contact faces;
    said contact faces being adjustably positionable about at least two axes and rotatable about at least one axis.

5. A support means as stated in claim 1 including
    actuator means carried by said cross-beam adapted to be operably coupled to and to actuate said hardness testing device.

6. A multipositionable support means for a hardness testing device for measuring the hardness of a surface in different positions, comprising:
    a pair of elongated support members having longitudinal axes;
    a cross-beam interconnecting said support members and slidably adjustable along said support members and adapted to selectively position said hardness testing device relative to a surface being tested;
    attaching means connected to each support member for selectively fixing one end of said support member relative to a surface being tested; and
    means carried by said cross-beam adapted to support said hardness testing device between said support members, including actuator means adapted to be operatively coupled to and to actuate said hardness testing device.

7. The invention as defined in claim 6 wherein each of said attaching means is pivotally mounted about an axis extending laterally with respect to the axis of the support member to which it is connected.

8. The invention as defined in claim 6 wherein each of said attaching members is rotatable about the axis of its associated support member.

* * * * *